US006652470B2

United States Patent
Patton et al.

(10) Patent No.: US 6,652,470 B2
(45) Date of Patent: *Nov. 25, 2003

(54) USING IMAGE MODIFICATION AND TEMPERATURE BIOFEEDBACK TO DIAGNOSE AND TREAT ADHD

(75) Inventors: David L. Patton, Webster, NY (US); Richard N. Blazey, Penfield, NY (US); Peter A. Parks, Topeka, KS (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/747,216

(22) Filed: Dec. 21, 2000

(65) Prior Publication Data

US 2003/0070685 A1 Apr. 17, 2003

Related U.S. Application Data

(63) Continuation-in-part of application No. 09/597,610, filed on Jun. 20, 2000, now Pat. No. 6,394,963.

(51) Int. Cl.[7] .............................................. A61B 5/00
(52) U.S. Cl. ........................ 600/549; 600/300; 128/898
(58) Field of Search .............................. 600/26–28, 300, 600/549, 558, 559; 128/897, 898, 905, 920; 434/236, 262

(56) References Cited

U.S. PATENT DOCUMENTS

| 5,377,100 A | | 12/1994 | Pope et al. ............... 600/545 |
| 5,465,729 A | * | 11/1995 | Bittman et al. ........... 600/545 |
| 5,725,472 A | * | 3/1998 | Weathers ................... 600/21 |
| 5,913,310 A | | 6/1999 | Brown ..................... 128/897 |
| 5,918,603 A | | 7/1999 | Brown ..................... 128/897 |
| 5,940,801 A | | 8/1999 | Brown ....................... 705/2 |
| 5,947,908 A | * | 9/1999 | Morris ..................... 600/484 |
| 6,053,739 A | | 4/2000 | Stewart et al. ............ 434/236 |
| 6,097,980 A | | 8/2000 | Monastra et al. ......... 600/544 |
| 6,102,846 A | * | 8/2000 | Patton et al. .............. 600/26 |
| 6,325,763 B1 | * | 12/2001 | Pfeiffer et al. ........... 600/549 |
| 6,394,963 B1 | * | 5/2002 | Blazey et al. ............. 600/549 |

FOREIGN PATENT DOCUMENTS

WO    WO 00/16687    3/2000

OTHER PUBLICATIONS

"Discourse on the Development of EEG Diagnostics and Biofeedback for Attention–Deficit/Hyperactivity Disorders", by: Joel F. Lubar, Biofeedback and Self–Regulation, vol. 16, No. 3, 1991.

"Spontaneous skin temperature oscillations in normal human subjects", by: Vladimir Shusterman et al., The American Physiological Society, 1997.

"Functional deficits in basal ganglia of children with attention–deficit/hyperactivity disorder shown with functional magnetic resonance imaging relaxometry", by: Martin H. Treicher et al., Nature Medicine, vol. 6, No. 4, Apr. 2000.

* cited by examiner

*Primary Examiner*—Charles A. Marmor, II
(74) *Attorney, Agent, or Firm*—Clark & Elbing LLP

(57) ABSTRACT

A method of reducing the symptoms of an individual having Attention Deficit Hyperactivity Disorder (ADHD) comprising: displaying an image, having a level of obscuration, to an individual with the symptoms of ADHD; sampling the peripheral skin temperature of the individual to provide sampled peripheral skin temperature data and reducing the level of obscuration of the image as a function of the sampled peripheral skin temperature data in order to minimize the symptoms of ADHD.

17 Claims, 13 Drawing Sheets

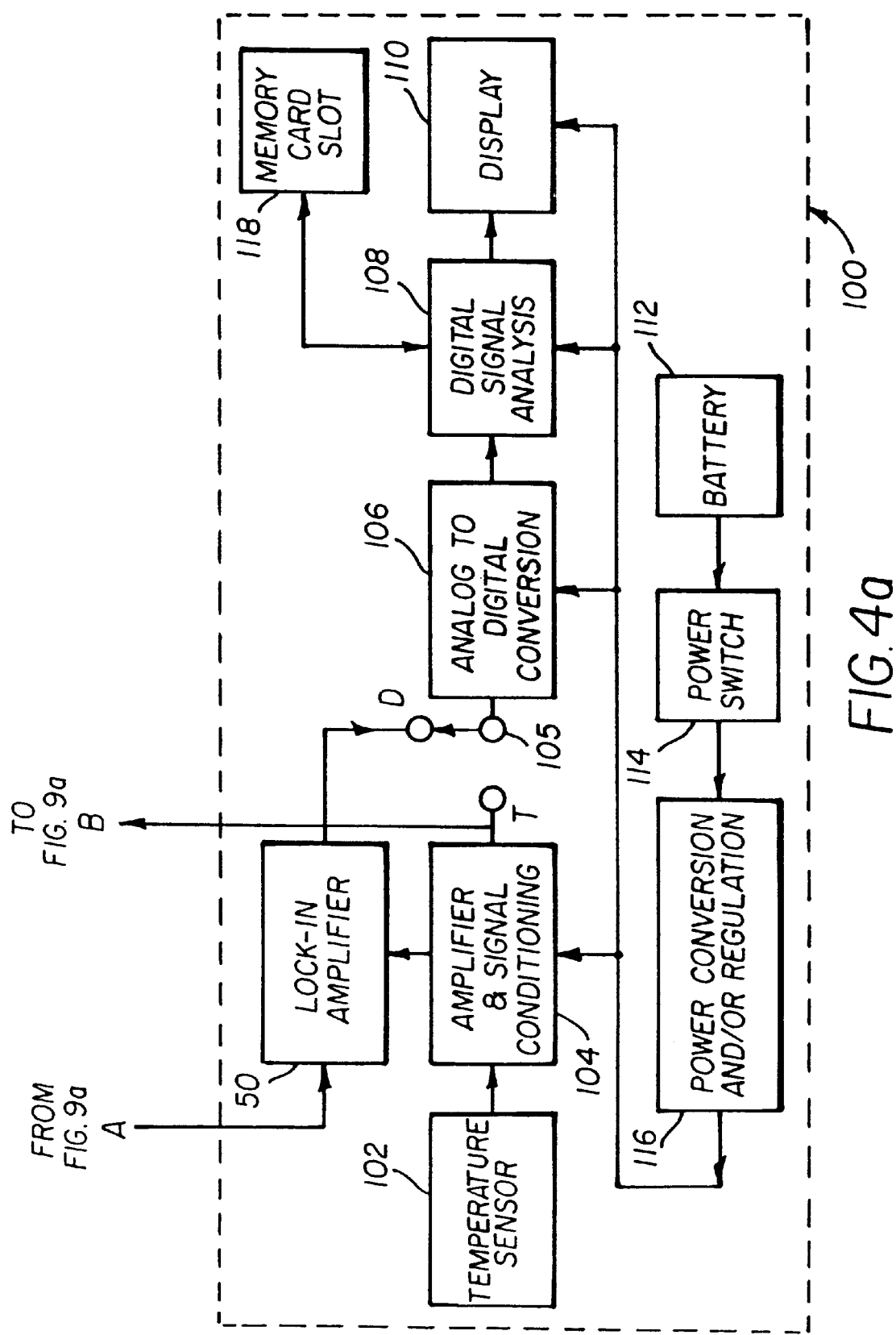

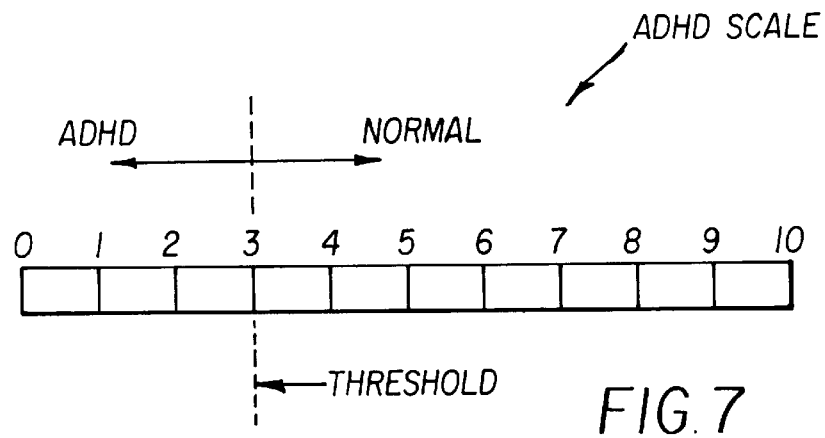
FIG. 7
| DATE | TIME | | |
|---|---|---|---|
| 6/13/00 | 8:00 AM | 2.8 | 0.65 |
| 6/13/00 | 12:00 NOON | 2.7 | 0.67 |
| 6/13/00 | 5:00 PM | 3.1 | 0.65 |
| 6/14/00 | 8:00 AM | 2.9 | 0.65 |
| 6/14/00 | 12:00 NOON | 2.8 | 0.66 |
| 6/14/00 | 5:00 PM | 3.0 | 0.68 |
FIG. 8
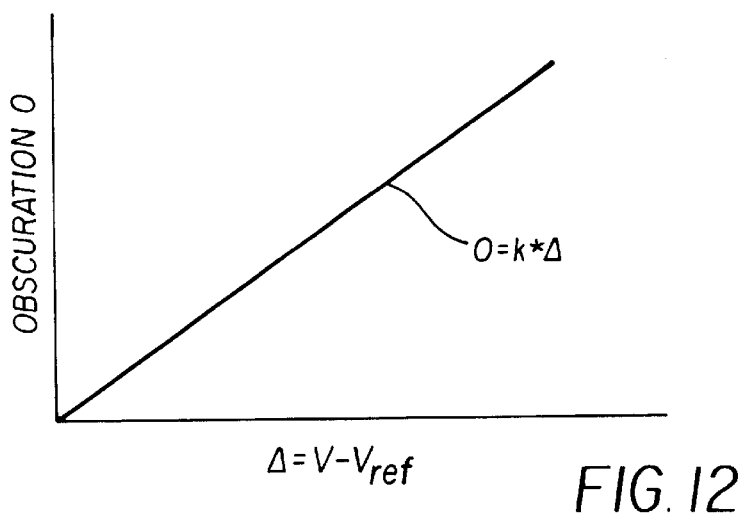
FIG. 12

USING IMAGE MODIFICATION AND TEMPERATURE BIOFEEDBACK TO DIAGNOSE AND TREAT ADHD

CROSS REFERENCE TO RELATED APPLICATIONS

This Continuation-in-Part patent application claims the benefit under 35 USC §120 of the earlier filing date of U.S. patent application Ser. No. 09/597,610, filed Jun. 20, 2000 now U.S. Pat. No. 6,394,963.

FIELD OF THE INVENTION

This invention relates in general to a technique for diagnosing and treating Attention Deficit Hyperactivity Disorder (ADHD) and more particularly to a technique for modifying a person's behavior using biofeedback and image modification.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is a difficult disorder to diagnose. The core symptoms of ADHD in children include inattention, hyperactivity, and impulsivity. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, learning disabilities).

Diagnosis of ADHD involves a process of elimination using written and verbal tests. However, there is no one objective, independent valid test for ADHD. Various objective techniques have been proposed but have not yet attained acceptance. These include:

1. The eye problem called convergence insufficiency was found to be three times more common in children with ADHD than in other children by University of California, San Diego researchers.

2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).

3. Techniques based on EEG biofeedback for the diagnoses and treatment of ADHD are described by Lubar (*Biofeedback and Self-Regulation*, Vol. 16, No. 3, 1991, Pages 201–225).

4. U.S. Pat. No. 6,097,980, issued Aug. 1, 2000, inventor Monastra et al, discloses a quantitative electroencephalographic process assessing ADHD.

5. U.S. Pat. No. 5,913,310, issued Jun. 22, 1999,inventor Brown, discloses a video game for the diagnosis and treatment of ADHD.

6. U.S. Pat. No. 5,918,603, issued Jul. 6, 1999, inventor Brown, discloses a video game for the diagnosis and treatment of ADHD.

7. U.S. Pat. No. 5,940,801, issued Aug. 17, 1999, inventor Brown, discloses a microprocessor such as a video game for the diagnosis and treatment of ADHD.

8. U.S. Pat. No. 5,377,100, issued Dec. 27, 1994, inventors Pope et al., discloses a method of using a video game coupled with brain wave detection to treat patients with ADHD.

9. Dr. Albert Rizzo of the Integrated Media Systems Center of the University of Southern California has used Virtual Reality techniques for the detection and treatment of ADHD.

10. U.S. Pat. No. 6,053,739, inventors Stewart et al., discloses a method of using a visual display, colored visual word targets and colored visual response targets to administer an attention performance test.

11. U.S. Pat. No. 5,377,100, issued Dec. 27, 1994, inventors Patton et al., discloses a system and method of managing the psychological state of an individual using images.

There are several clinical biofeedback and physiology monitoring systems (e.g. Multi Trace, Bio Integrator). These systems are used by professional clinicians. A clinician monitors a patient's physiologic changes and accordingly uses different protocols. Some multimedia content (e.g. images, sound) can be used during the session to display a patient's pattern of physiologic reactivity and to help the patient in his/her task defined by the clinician. A good example is a session designed to help a patient to increase her/his hand temperature. A synthetic animation with the sun rising over the ocean can be used to show the patient's temperature. When the patient's temperature increases the sun is rising over the water horizon. When his/her temperature decreases the sun is moving behind the horizon. A clinician can help the patient with verbal instructions. Although skin temperature spectral characteristics have been shown to indicate stress-related changes of peripheral vasomotor activity in normal subjects (See: "Spontaneous skin temperature oscillations in normal human subjects", by: Shusterman et al., pp. 1173–1181), there has been no disclosure of the use of variations in skin-temperature response to assist in diagnosing ADHD. (See: Biofeedback and Self-Regulation, Vol. 20, No. 4, 1995).

PCT International Application WO 00/16687, published Mar. 30, 2000, discloses a method and device for determining depth of anesthesia. A pattern of very low frequency oscillations in measured skin temperature is defined and analyzed. The frequency band width of a frequency domain analysis of the oscillatory pattern, or the correlation between simultaneous oscillatory patterns measured at different physical locations, are used separately or fused to obtain an index of depth of anesthesia. There is no disclosure of the use of variations in skin temperature response to assist in diagnosing ADHD.

As discussed above, the primary method for diagnosing ADHD is the use of a bank of written and verbal assessment instruments designed to assess criteria established by American Medical Association (AMA) as described in the Diagnostic and Statistics manual—IV (DSM-IV) and administered by the school psychologist or other licensed practitioner. In some cases those individuals who meet DSM-IV criteria for ADHD diagnosis are prescribed a drug such as Ritalin. Behavioral observations of the patient while on Ritalin are conducted to assess the impact of prescribed medication.

U.S. patent application Ser. No. 09/597,610, describes an apparatus and method of determining whether an individual has Attention Deficit Hyperactivity Disorder by analyzing physiologic reactivity patterns (lower average Mrange) when the subject is asked to sit quietly in a low stimulus environment for a short period of time.

There are many factors, which can contribute to a change in skin temperature variability besides ADHD. The largest potential source of error is stress due to causes other than the sensory deprivation included in the test. Other extraneous causes of reduced peripheral temperature variability (TV) might include disease states, room temperature variation, etc.

The primary feature of U.S. patent application Ser. No. 09/597,610 is to diagnose subjects with ADHD. There is no attempt made to treat the condition once it has been diagnosed.

SUMMARY OF THE INVENTION

According to the present invention, there is provided a solution to the problems and fulfillment of the needs discussed above.

According to a feature of the present invention, there is provided a method for providing biofeedback to the patient to indicate to the patient that they are indeed being effective in regulating the brain activity controlling their parasympathetic or sympathetic functions.

According to a feature of the present invention, there is provided a method of reducing the symptoms of an individual having Attention Deficit Hyperactivity Disorder (ADHD) comprising: displaying an image, having a level of obscuration, to an individual with the symptoms of ADHD; sampling the peripheral skin temperature of said individual to provide sampled peripheral skin temperature data;
 and reducing the level of obscuration of said image as a function of said sampled peripheral skin temperature data in order to minimize said symptoms.

ADVANTAGEOUS EFFECT OF THE INVENTION

The invention has the following advantages.

1. A technique for diagnosing ADHD is provided which is simple, inexpensive, reliable and provides a level of accuracy improved over the prior art.

2. A technique for treating ADHD is provided.

BRIEF DESCRIPTION OF THE DRAWINGS

FIGS. 4a and 4b are a block diagram of a system incorporating the present invention respectively in diagnosis and treatment modes.

FIG. 7 is a diagrammatic view useful in explaining the present invention.

FIG. 8 is a diagrammatic view useful in explaining the present invention.

FIG. 12 is a graphical view useful in explaining the present invention.

DETAILED DESCRIPTION OF THE INVENTION

According to the invention, it has been found that a signature of ADHD is hidden in fluctuation of the temperature of the skin as measured at the extremities such as at a fingertip. Biofeedback practitioners have long used measurement of hand temperature to help subjects manage their physiology by controlling blood flow to the extremities.

It is well known in the art that as person's stress level increases the blood vessels in the body contract as is evidenced by the fact a person's blood pressure increases as their level of stress increases. As the blood vessels in the body contract, blood flow is restricted. This is most evident in the extremities such as the fingers, because the blood vessels in the extremities are small and furthest from the heart. A direct result of decreased blood flow to the blood vessels in the extremities is a decrease in the peripheral temperature of the extremities. Conversely, as a person's stress level decreases and one relaxes, the blood vessels also relax and expand causing blood flow to increase. As the blood flow to the vessels in the extremities increases the peripheral temperature of the extremities increases. When a subject with ADHD is subjected to sensory depravation such as being made to look at a blank, screen or an obscured image, the lack of stimulation increases their level of anxiety and their stress level increases. As their stress level increases their blood vessels contract and the peripheral temperature of their extremities decreases. Conversely, as the screen or image they are viewing becomes less obscured or more interesting, thus decreasing their sensory depravation, their level of anxiety and stress decreases, thus relaxing the blood vessels, increasing the blood flow and raising the temperature of their peripheral temperature of the extremities.

Figure 1:
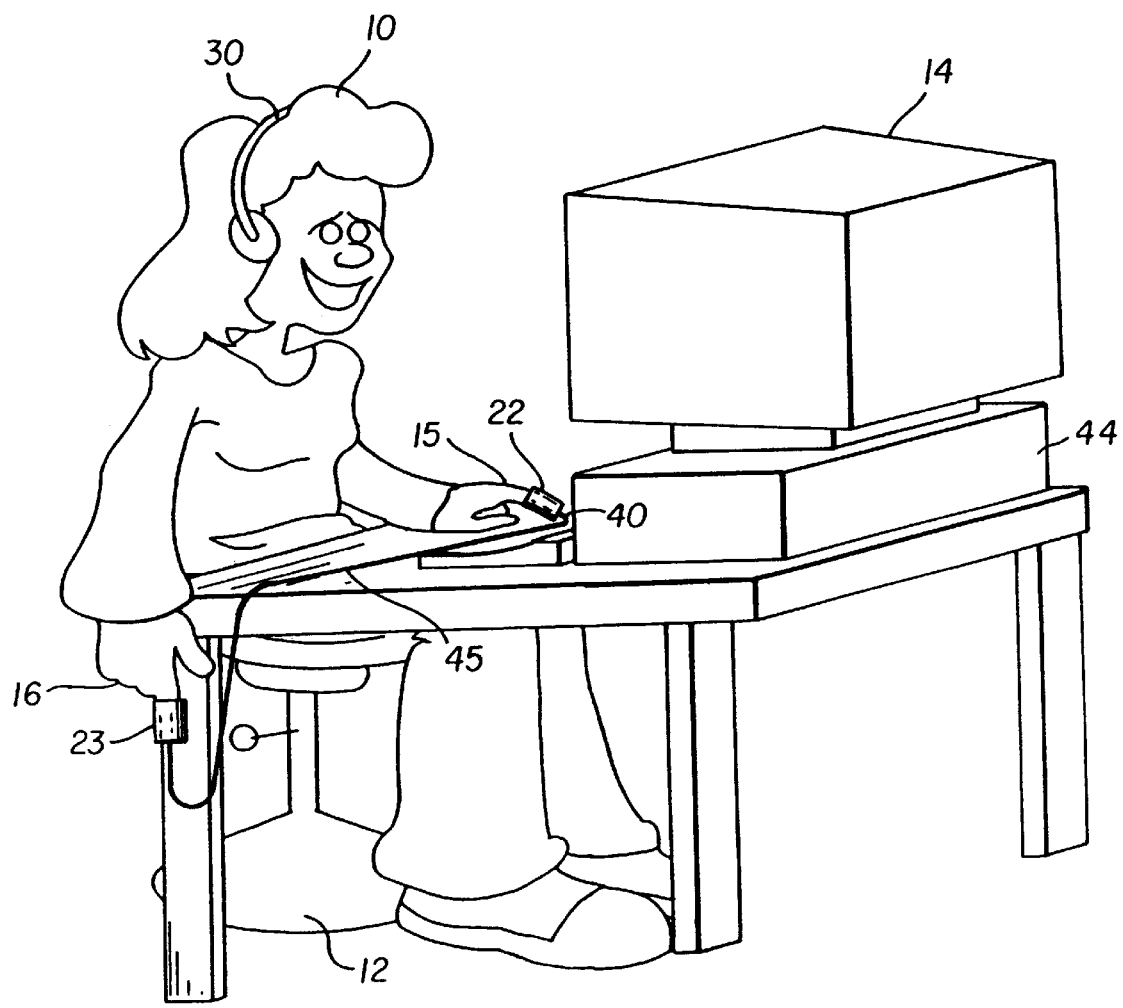
FIG. 1 is a diagrammatic view illustrating an embodiment of the present invention.

As shown in FIG. 1, a subject 10 is sitting on a chair 12 viewing a display device 14 wearing a set of earphones 30 connected via a wire not shown to a sound-generating device. In the embodiment shown the sound may be generated using an external CPU 44. The subject 10 is at rest in an inactive state viewing the display device 14. The subject's 10 skin temperature is measured via a finger temperature sensor module 22 mounted on the subject's finger on their left hand 15 connected via a wire 40 to an external CPU 44. In the embodiment shown the temperature sensor module 22 is connected to the external CPU 44, which can be used as the control and recording device portion.

Figure 2:
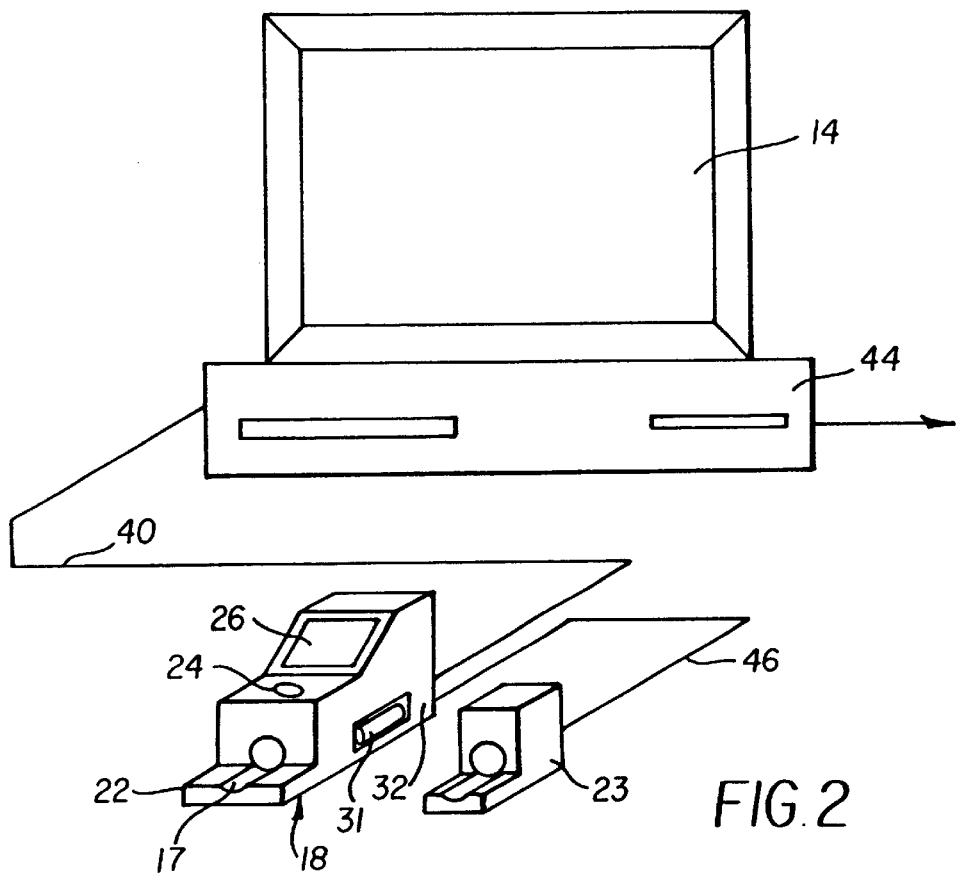
FIG. 2 is a perspective view showing in greater detail the embodiment of FIG. 1.

Referring to FIG. 2, the analyzer 18 may be a stand-alone device having the temperature sensor module 22 as an integral part. The analyzer 18 has a display 26 (such as an OLED) or may be connected to an external display 14. The display 14 can be a monitor, television, palm pilot, or any other type of soft display or device with a soft display.

Referring again to FIG. 1, the subject's 10 skin temperature is measured by a temperature sensor module 23 mounted on the subject's right finger 16 connected via a wire 45 to the external CPU 44 The subject's 10 temperature may be measured using either the finger tip 15 or the fingertip on the right hand 16 or fingertips on both hands. The external CPU 44 is connected to the display device 14. The earphone 30 may be used to block out ambient noise, to produce a white noise intended to reduce or eliminate the audio stimulus from the environment during the test or to obscure a sound related to an image shown on the display 14. The sound generated may be synchronized with what is appearing on the display 14.

Referring to FIG. 2, there is shown an illustration of the analyzer 18 comprising temperature sensor modules 22 and 23, where the subject 10 inserts their left fingertip 15 in groove 17. The temperature sensor 22 can have an on/off switch 24, and a display 26. The temperature sensor module 22 can have an internal power supply, such as a battery 31, or an external low voltage power supply port 32 for an external low voltage power supply (not shown), such as used for a telephone. The temperature module 22 can be connected to the external CPU 44 via a cable 40 (such as an USB or RS 232 cable), or wireless-transmitting device such as a RF or JR link (not shown). A second temperature sensor module 23 can be connected to the external CPU 44 or the analyzer 18 via a cable 46. The second temperature sensor module 23 can be used to sample the skin temperature of the right hand. It should be understood that either temperature sensor module might be used on either hand. Analyzer 18 or CPU 44 applies the appropriate transforms to analyze the sampled temperatures and displays the results on the display 14 or 26. The results from the test can be stored in the CPU's memory (not shown) and can be transmitted via a transmission link such as the Internet to other locations.

Figure 3:
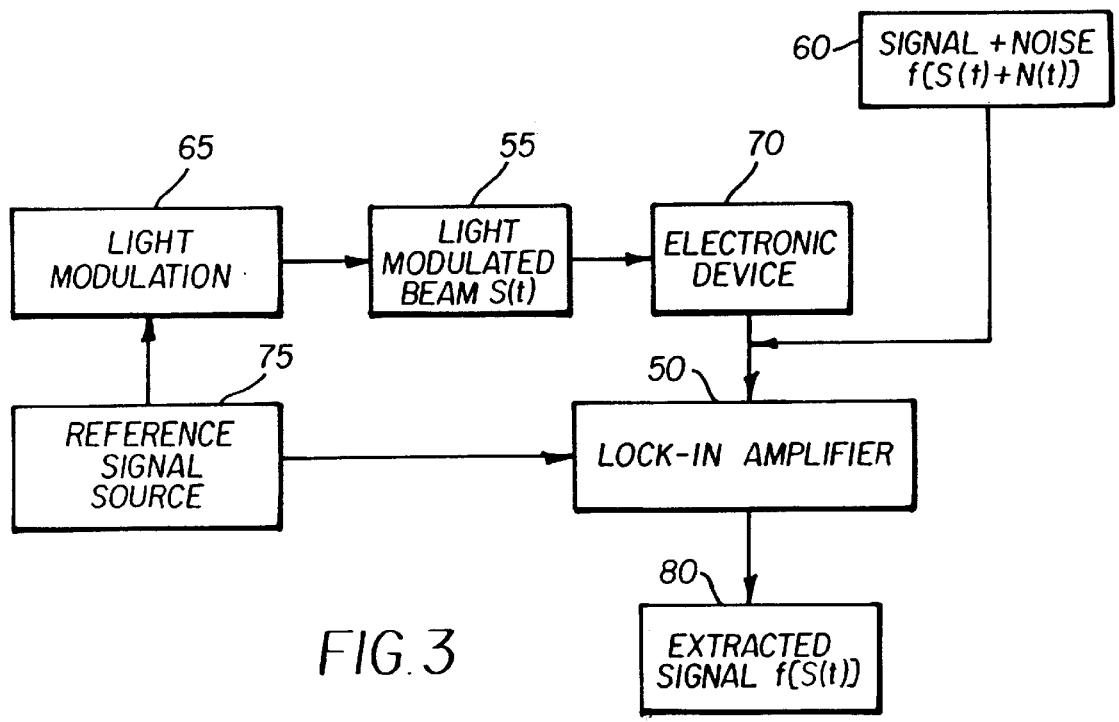
FIG. 3 is a block diagram illustrating the function of a Lock-in Amplifier.

Now referring to FIG. 3, there is provided a block diagram showing how a signal S (t) 55 which is combined with a much larger noise N (t) 60, can nevertheless be extracted by a lock-in amplifier if that signal is modulated with a known reference. An example is a light beam modulated by a chopper 65. The light is then incident on an electronic device 70 and an output electrical signal is collected. That electronic signal contains within it a signal synchronous with the light modulation, but at a level many orders of magnitude weaker than other components in the electronic device output (the Noise). When the output of the electronic device 70 and the reference signal 75 are fed to a lock-in amplifier 50, the signal can be extracted 80. Examples of lock-in amplifiers 50 are the Dual Phase Lock-in Amplifier Printed Circuit Model 5105 or the Dual Phase Wide Bandwidth DSP Lock-in Amplifier Model 7280 made by Perkin-Elmer Corp.

Referring now to FIG. 4a, analyzer module 18 includes circuit 100. The circuit 100 includes a temperature sensor 102, lock-in amplifier 50, amplifier and signal conditioner 104, a switch 105 (shown in the diagnosis (D) position), analog to digital converter 106, digital signal analysis 108, display 110, battery 112, power switch 114 and power conversion and/or regulation 116. The circuit 100 can include a memory card slot 118 for receiving a memory card, which can provide system upgradability, and removable data export without compromising safety isolation.

Referring again to FIG. 1, the fingertip temperature is first recorded during an interval when the subject 10 has been asked to sit quietly for a given period of time, nominally about 10 minutes while viewing monitor 14. The monitor is either blank or the scene appearing on the monitor is obscured or distorted. The time period may be shorter or longer. The temperature data is sampled via circuit 100 (shown in FIG. 4a) at a time interval $\Delta t$ creating a list of N temperature samples, which are digitized by A/D 106 and which are stored. The N samples are divided into windows of m samples. The data from each window is then passed through a Fast Fourier Transform (FFT) algorithm in circuit 108 producing $2^{m-1}$ data points spaced equally in frequency space. The values are complex numbers having form $$FFT(f_n)=A(f_n)+B(f_n)i$$

where i is the $\sqrt{-1}$. The Phase $\Phi(f_n)$ can be found from the equation $$\Phi(f_n) = \text{Tan}^{-1}\left(\frac{B(f_n)}{A(f_n)}\right)$$

and the Magnitude $M(f_n)$ from $$M(f_n)=\sqrt{B(f_n)^2+A(f_n)^2}$$

Figure 5:
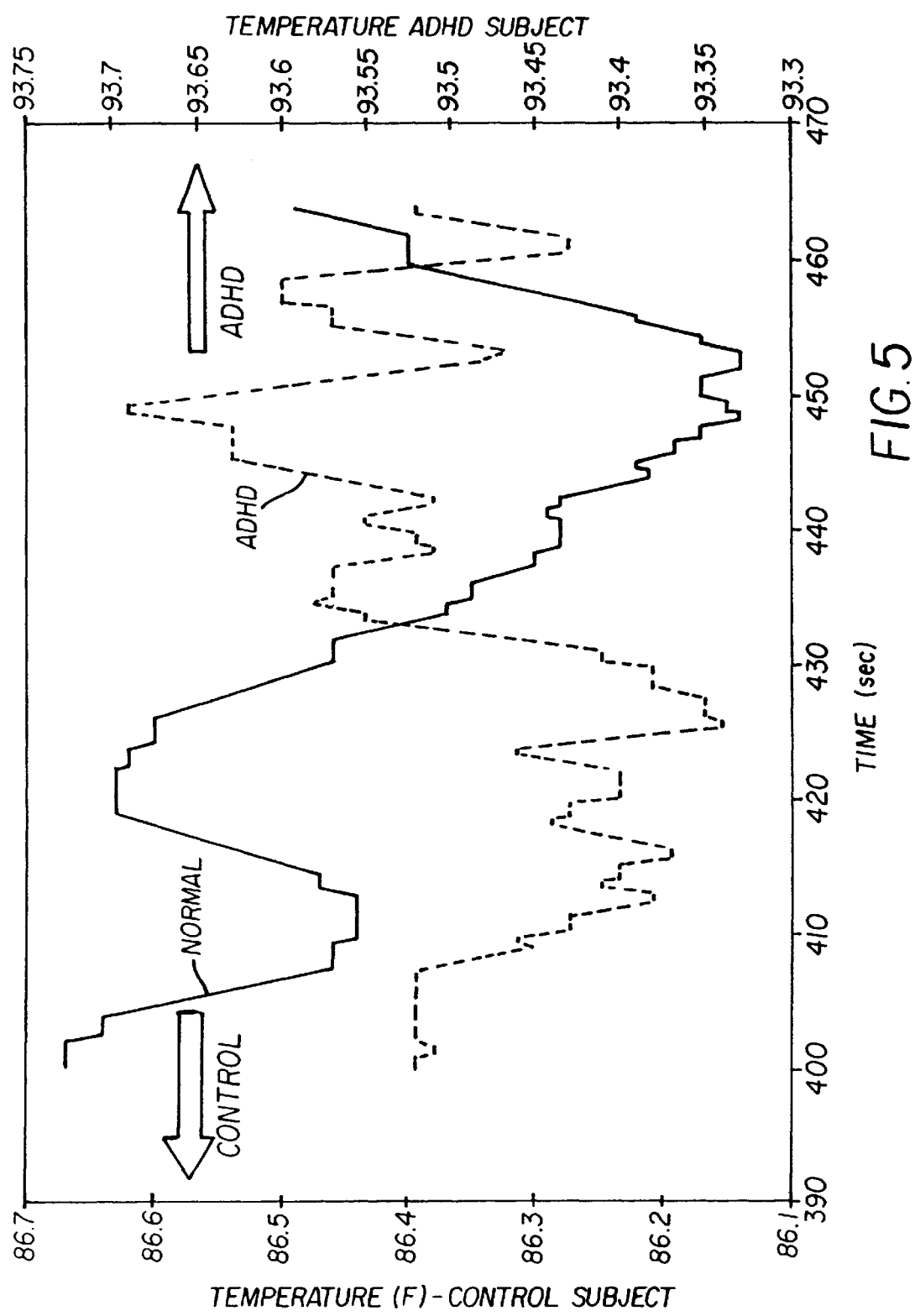
FIGS. 5, 6a and 6b are graphical views useful in explaining the present invention.

FIG. 5 graphically illustrates the temperature signal during one window for a normal subject and a person diagnosed with ADHD.

Figure 6A:
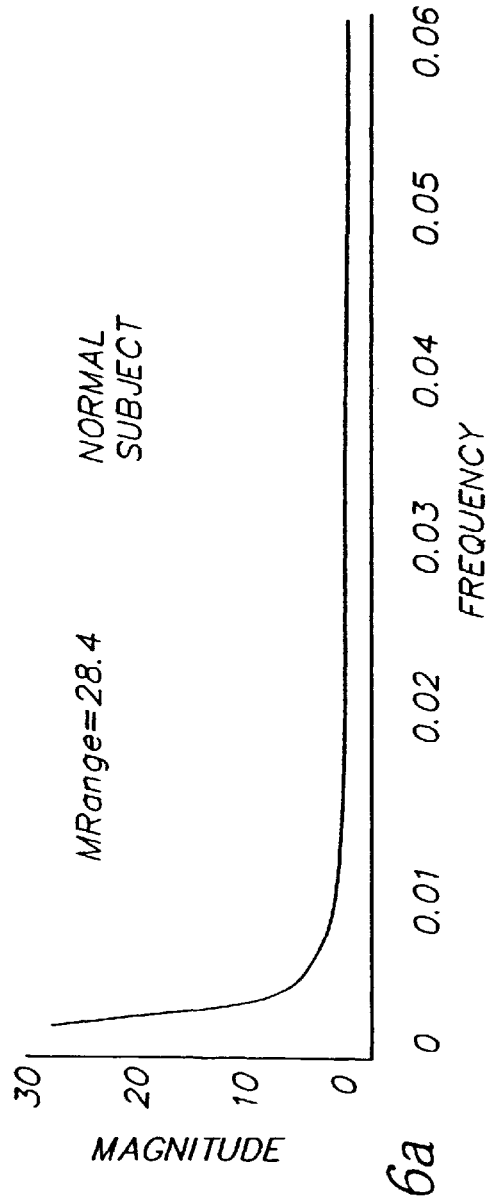
Figure 6B:
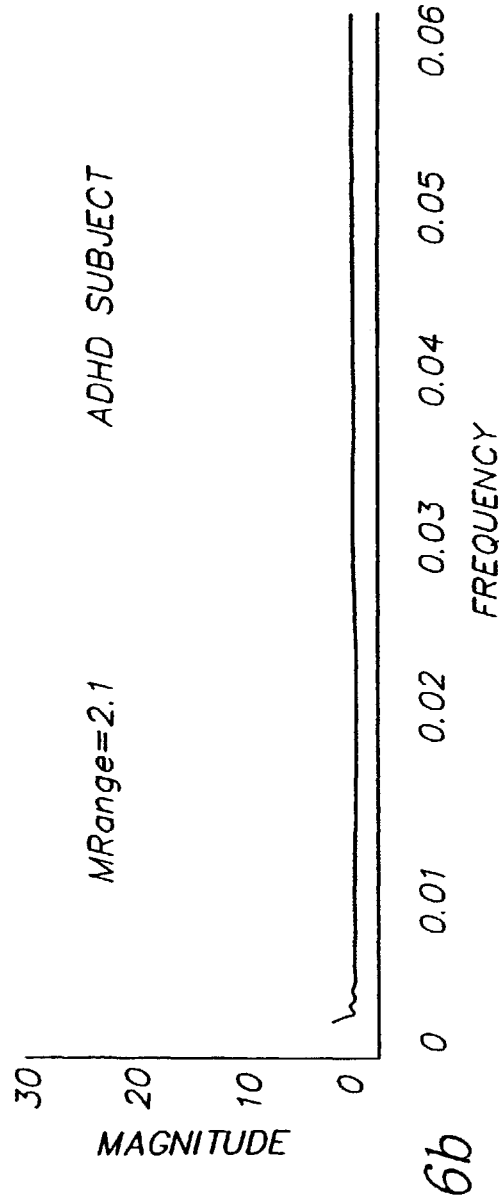

FIGS. 6a and 6b graphically illustrate the magnitude transform for the data corresponding with a subject with ADHD and a normal subject. The magnitude spectrum undergoes dramatic changes essentially changing from a hyperbolic curve to a flat response. These graphical illustrations as well as the following can be displayed on display 110 or on some other visual indication device.

The following is another feature of the present invention:

Raw Data

The raw data $T_{i,k}(t)$ is the temperature taken at a fingertip during the baseline period.

Windows

The data for each session were divided into a series of windows prior to performing the Fourier Transform operation. Call the window width w. For each window a FFT algorithm calculates the Fourier Transform F(f). The Magnitude and Phase of this transform are defined as given above. The range of magnitude variation during a window is given below where $f_{max}$ and $f_{min}$ are the frequencies where the Magnitude is the greatest and the least respectively (note the dc component at frequency zero is excluded).

$$M_{range}=[M(f_{max})-M(f_{min})]$$

Session Mean and Standard Deviation

The mean magnitude range for subject i during session k is found from equation 1.0. where m is the number of windows in the session.

$$<M_{i,k}> = \frac{\sum_{j=1}^{m} [M(f_{\max})_j - M(f_{\min})_j]}{m} \quad (1.0)$$

And the corresponding standard deviation is:

$$<s_{i,k}> = \sqrt{\frac{\sum_{j=1}^{m} \{[M(f_{\max})_j - M(f_{\min})_j] - <M_{i,k}>\}^2}{m-1}} \quad (1.1)$$

Determination Indicator

Positive diagnostic indicator is established based upon the chart of FIG. 7 by setting a threshold level (e.g., 3) for one of the parameters. Below that limit, the subject has a positive diagnostic indicator for ADHD. Above the limit, the subject has a negative diagnostic indicator for ADHD. This procedure can be improved by taking peripheral temperatures during different times of the day over a period of one or more days. FIG. 8 shows the results taken at different times of the day over a period of two days.

Figure 9A:
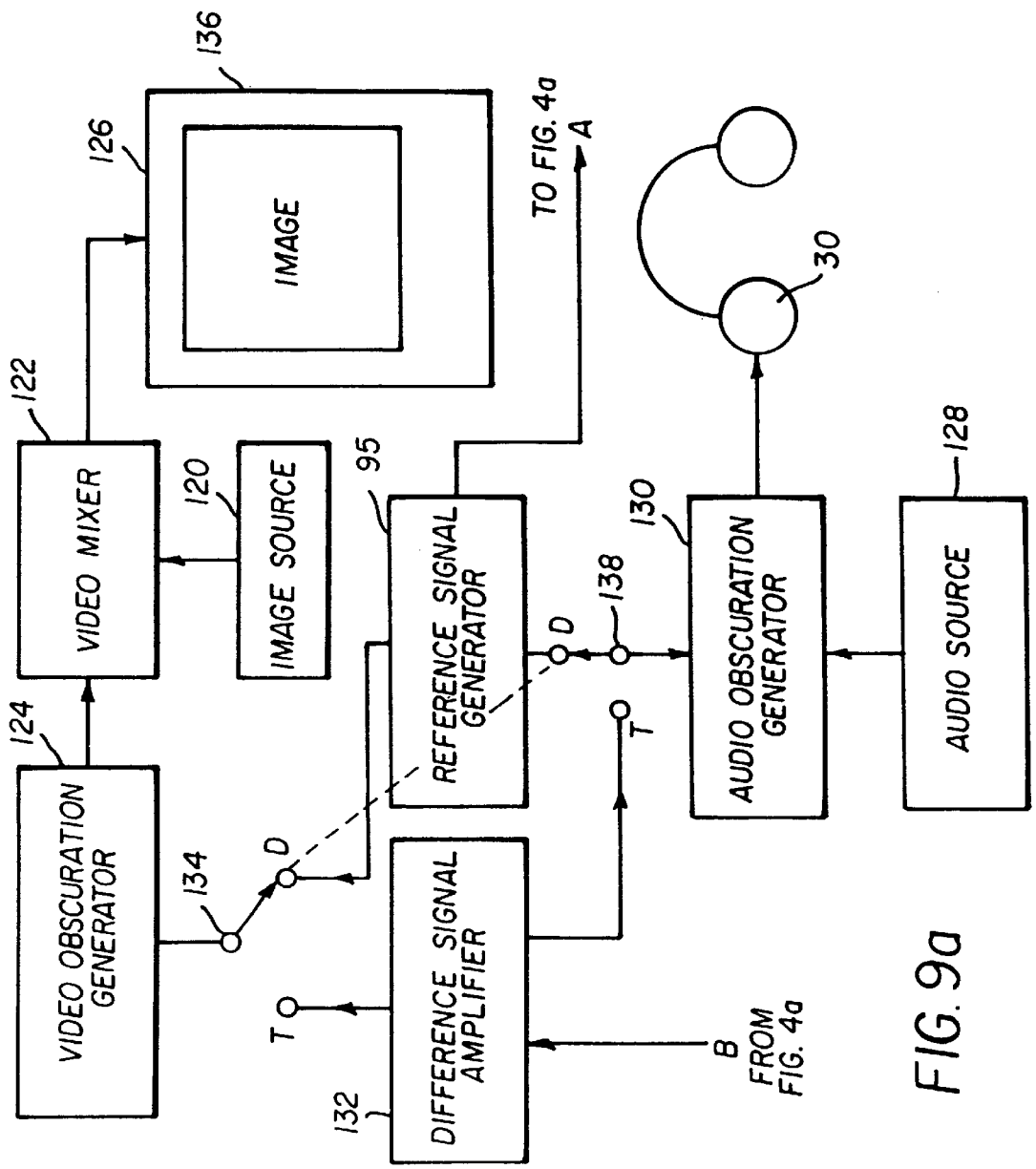
FIGS. 9a and 9b are a block diagram of a system incorporating the present invention respectively in diagnosis and treatment modes.

Referring to FIG. 9a, with switches 134 and 138 set to the diagnostic mode D, an image source 120 sends a digitized image to a video mixer 122 where it is mixed with varying amounts of obscuration from the video obscuration signal generator 124. The obscured image's signal is then fed to monitor 126. The amount of obscuration is synchronized to a reference supplied by signal generator 95, which may be any common waveform such as sine wave, square wave, ramp, triangle wave etc. Simultaneously, an audio source 128 may be fed through an audio obscuration generator 130 where it is mixed with audio noise or attenuated in proportion to and in synchronism with the reference signal. Both the visual and auditory stimuli supplied to the subject are modulated by the reference signal from the reference signal generator 95.

Figure 11A:
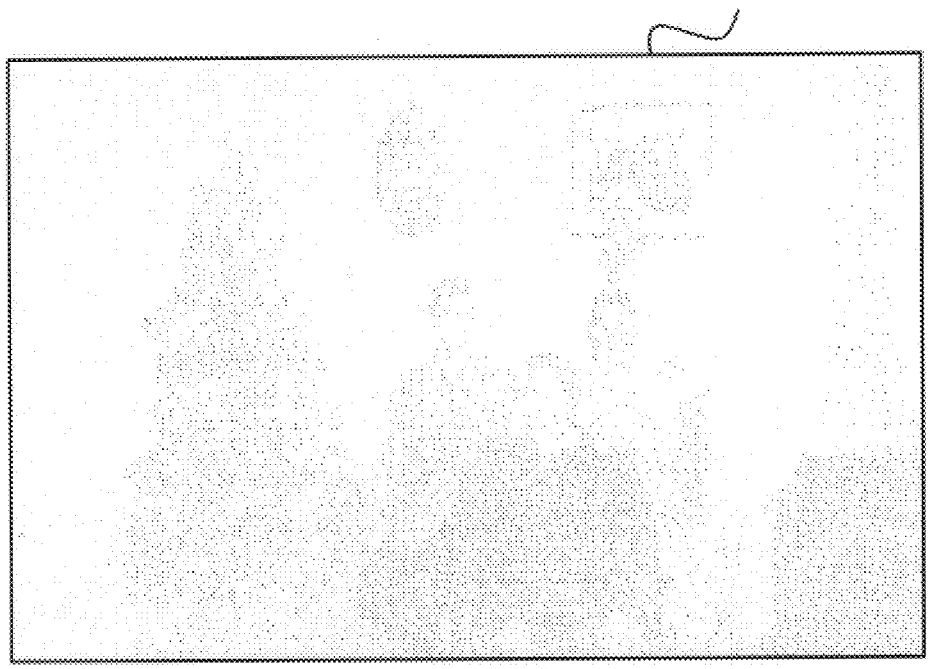
FIG. 11a is an image as it is displayed on a monitor in accordance with the present invention.
Figure 11B:
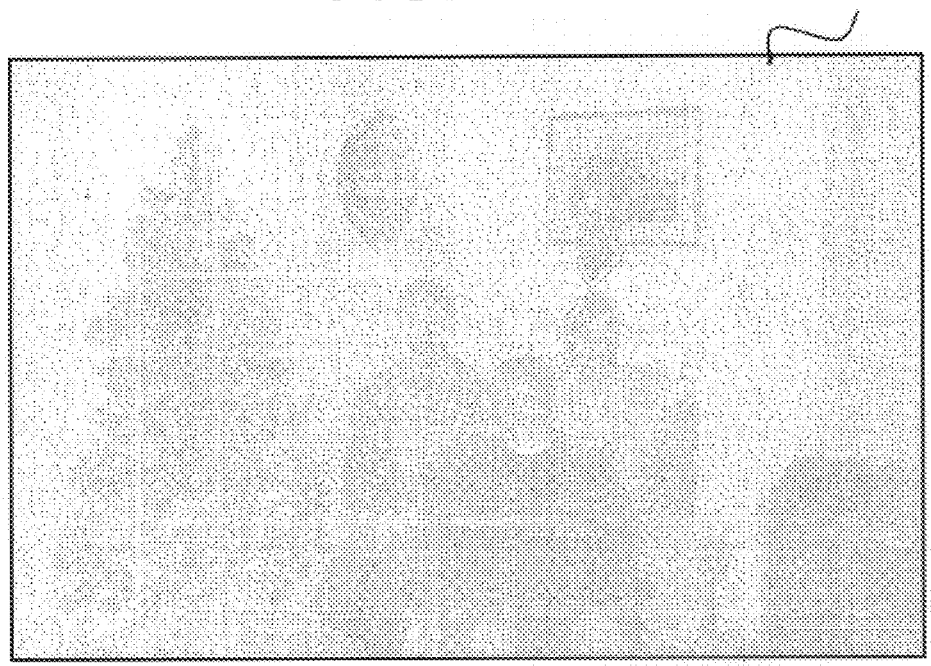
FIG. 11b is an image as it is displayed on a monitor in accordance with the present invention.
Figure 11C:
FIG. 11c is an image as it is displayed on a monitor in accordance with the present invention.
Figure 11D:
FIG. 11d is an image as it is displayed on a monitor in accordance with the present invention.
Figure 11E:
FIG. 11e is an image as it is displayed on a monitor in accordance with the present invention.
Figure 11F:
FIG. 11f is an image as it is displayed on a monitor in accordance with the present invention.

Referring now to FIGS. 11a, b, c, d, e, and f, the technique previously described can be used to extract a subject's response to modulated sensory depravation. By changing (FIG. 9a) the amount of obscuration of a stimulating image 200a, b, c, d, e, and f and/or an audio signal, modulation of the subject's physiology, as measured by variation of his/her peripheral temperature is created.

Referring to FIG. 4a, the peripheral temperature as measured by the temperature sensor 102, or a function derived from the subject's peripheral temperature, is fed from amplifier and signal conditioner 104 to the lock-in amplifier 50. The reference signal 75 is fed from the reference signal generator 95 (shown in FIG. 9a) to the lock-in amplifier 50 from point A. With switch 105 set in the diagnostic mode D the part of the subject's physiological response which is synchronous with the reference signal 75 is extracted by circuit 100, thus detecting a subject response which is directly correlated with the sensory depravation signal and uncontaminated by other physiological responses.

Figure 10:
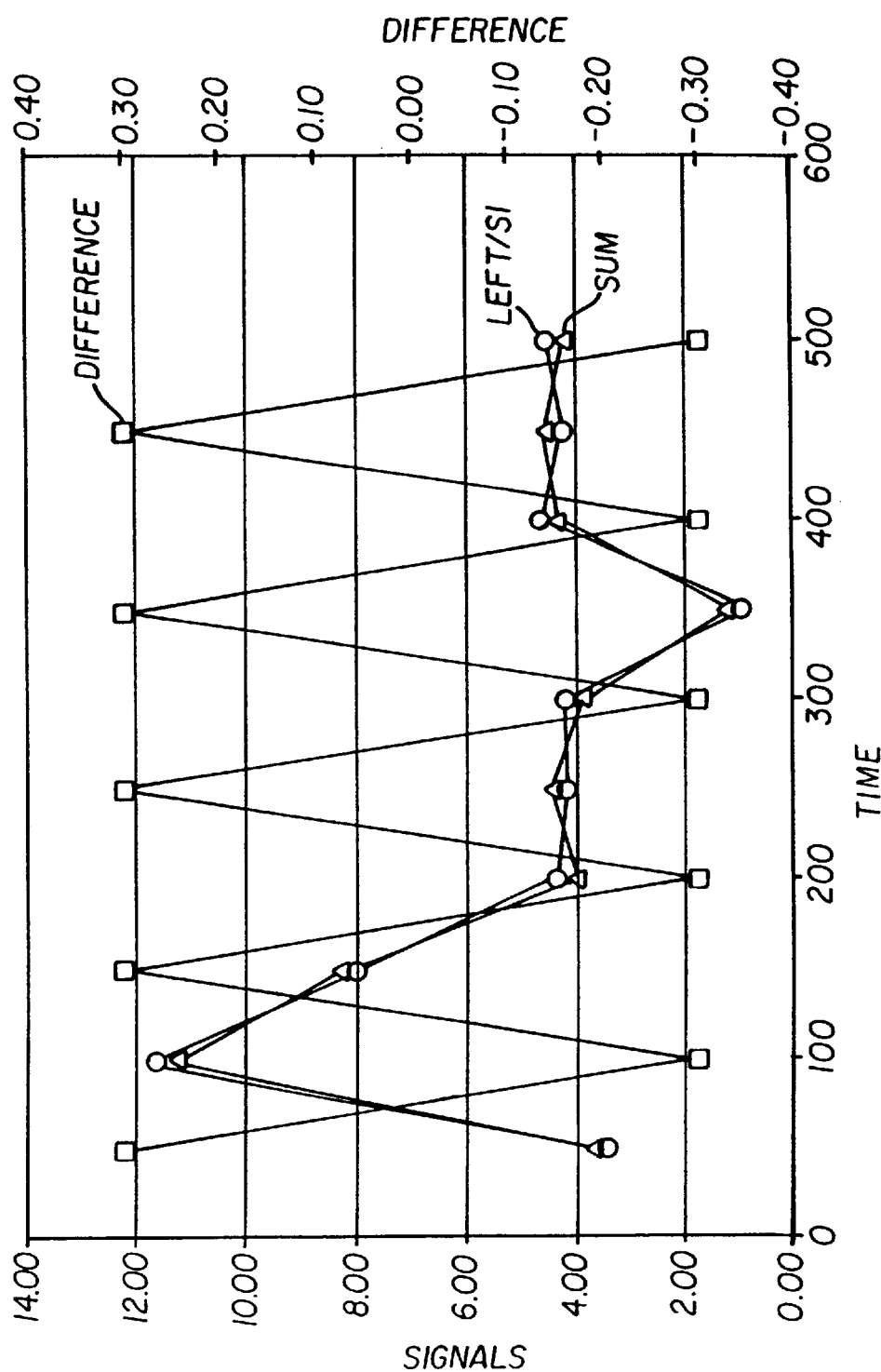
FIG. 10 is a diagrammatic view useful in explaining the present invention.

Now referring to FIG. 10, the results are shown where a small modulation has been added to actual Mrange data for a subject. FIG. 10 shows the original signal (diamonds), the signal with the modulation added (triangles) and the signal that would be extracted (X's). Even though only a very small extracted signal (right hand axis) of the subject's temporal variation could be attributed to the sensory depravation it is still detectable. In this example the reference-modulated component is a constant 0.3 units on a signal whose average value is about 5.0 or about 6%.

Referring to FIG. 1, an image 200a shown in FIG. 1a is displayed on the screen 14. As the subject 10 concentrates on the image 200a the blood flow to the fingertip 15 and/or 16 increases causing the subject's 10 peripheral temperature to change.

Figure 4B:
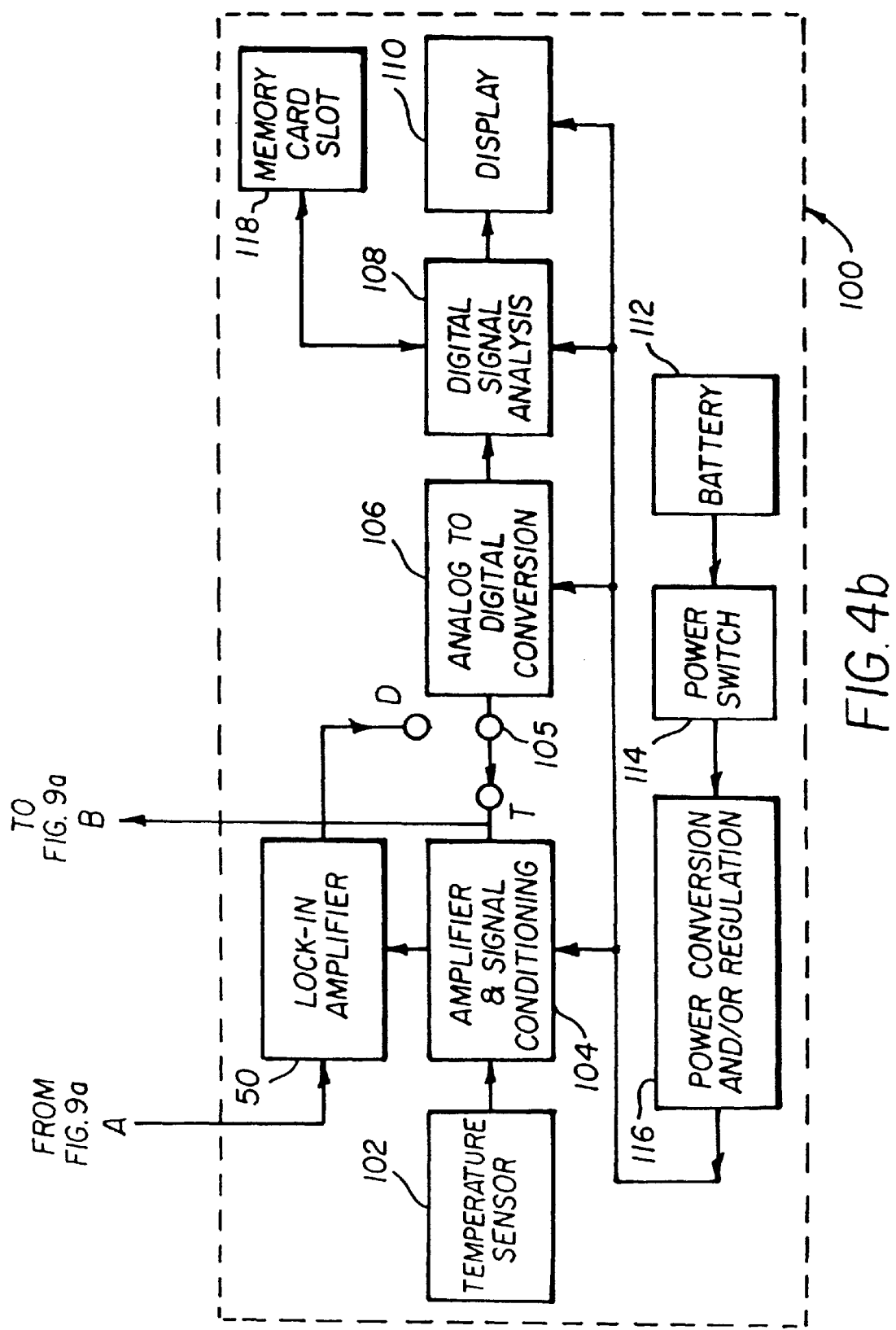
Figure 9B:
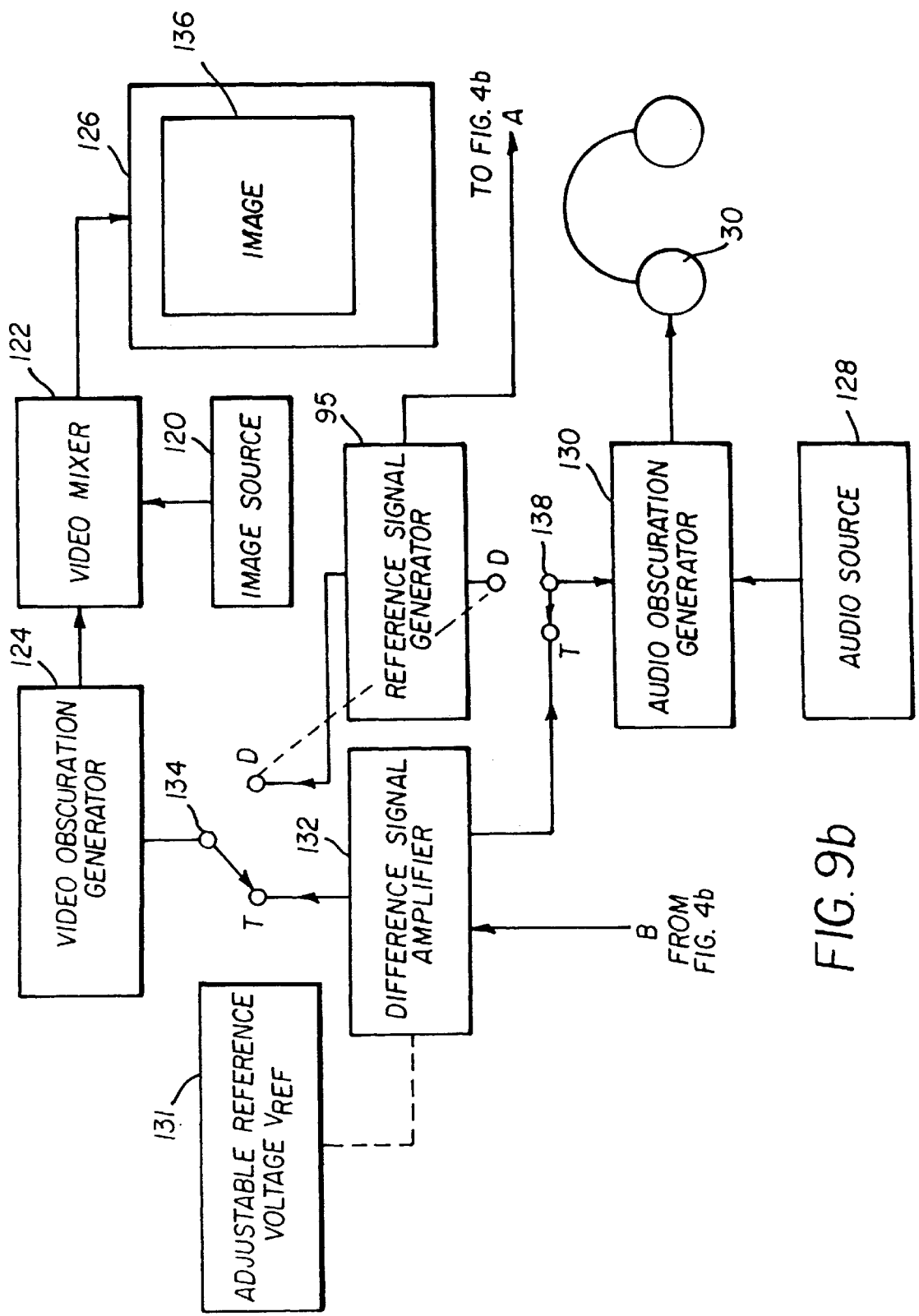

Referring to FIG. 4b, with switch 105 set in the treatment mode T the change in the subject's peripheral temperature is fed from the amplifier and signal conditioner 104 of circuit 100 at point B to the difference signal amplifier 132 shown in FIG. 9b. The change in the subject's peripheral temperature is also fed from the amplifier and signal conditioner 104 through the analog to digital converter 106, to the digital signal analysis 108 where the result is shown on display 110.

Now referring to FIG. 9b, with switches 134 and 138 set in the treatment mode T the difference signal amplifier 132 compares signal B, which is a measure of the subjects peripheral temperature, to an adjustable reference voltage $V_{ref}$(131) which may be generated internally to 132 or supplied externally. The value of $V_{ref}$ is linearly related to the desired peripheral temperature. Suppose, for example, the subject's peripheral temperature was 72 F. If the value $V_{ref}$ was then set to correspond to a temperature of 90 F., the difference amplifier output would then be proportional to the difference between these temperatures (18 F.).

The obscuration generators 124 and 130 would be so constructed that the amount of obscuration would be proportional to the size of the difference signal as shown in FIG. 12.

Now referring to FIG. 12, the obscuration O shown on the ordinate is directly proportional to the difference voltage $\Delta = V - V_{ref}$ shown on the abscissa as indicated by the equation $O = k^* \Delta$ Thus, as the subject's peripheral temperature approached the reference temperature, the difference signal would also decrease causing a proportional decrease in the obscuration level. When the subject's temperature reached the reference setting of 90 degrees, the obscuration would vanish and the scene would be clearly visible and the audio clearly heard.

Referring to FIGS. 9a and 9b, the switch 134 switches the input of the video obscuration signal generator 124 from the reference signal generator 95 to the difference signal amplifier 132. The image 136 can be the same as the image 200a shown in FIG. 11a. As previously described in FIG. 9b, the image 136 is modified in relationship to changes in the subject's 10 peripheral temperature. For example the image 200a can be a scene obscured by fog. As the subject concentrates on the image the fog begins to gradually disappear until the scene becomes clear as shown in FIGS. 11a through 11f and images 200a through 200f respectively. This technique is used to train the subject 10 to modify his or her behavior. Likewise switch 138 can switch the input of the audio obscuration signal generator 130 from the reference signal generator 95 to the difference signal amplifier 132 causing the audio heard through the earphones 30 to be modified in relationship to the subject's 10 peripheral temperature. As in the case of the image the sound for example may be made louder or a distortion such as white noise may be reduced so the audio becomes clearer.

The invention has been described in detail with particular reference to certain preferred embodiments thereof, but it will be understood that variations and modifications can be effected within the spirit and scope of the invention.

PARTS LIST 10 human subject
12 chair
14 display
15 left fingertip
16 right fingertip
17 groove
18 analyzer
22 temperature sensor module
23 temperature sensor module
24 on/off switch 26 display
30 earphones
30 battery
31 low voltage power supply port
40 cable
44 CPU
45 cable
46 cable
50 lock-in Amplifier
55 signal S(t)
60 noise signal N(t)
65 modulated light beam
70 electrical device
75 reference signal
80 extracted signal f (S (t))
95 reference signal generator
100 circuit
102 temperature sensor
104 signal conditioner
105 switch
106 A/D converter
108 digital signal analysis
110 display
112 battery
114 power switch
116 power conversion and/or regulation
118 memory slot
120 image source
122 video mixer
124 video obscuration generator
126 monitor
128 audio source
130 audio obscuration generator
131 $V_{ref}$
132 difference signal amplifier
134 switch
136 image
138 switch
200a image
200b image
200c image
200d image
200e image
200f image

What is claimed is:

1. A method of reducing the symptoms of an individual having Attention Deficit Hyperactivity Disorder (ADHD) comprising:

displaying an image, having a level of obscuration, to an individual with the symptoms of ADHD;

sampling the peripheral skin temperature of said individual to provide sampled peripheral skin temperature data; and reducing the level of obscuration of said image as a function of said sampled peripheral skin temperature data in order to minimize said symptoms.

2. The method of claim 1 wherein said symptoms of said individual are manifested by a peripheral skin temperature that is less than a desired value and wherein said level of obscuration of said image is reduced as the difference between peripheral skin temperature of said individual and said desired value is reduced.

3. The method of claim 1 wherein the skin temperature of at least one extremity of said individual is sampled.

4. The method of claim 1 wherein the skin temperature of at least one finger of said individual is sampled.

5. The method of claim 1 including providing obscured audio related to the displayed image to said individual; and wherein obscured audio is reduced as a function of said sampled peripheral skin temperature.

6. The method of claim 5 wherein said audio is provided to said individual by earphones worn by said individual.

7. The method of claim 1 wherein there is a linear relationship between said sampled skin temperature and level of obscuration of said image.

8. A system for reducing the symptoms of an individual having ADHD comprising:

a display;

an image source for images displayed on said display;

a device for sampling the peripheral skin temperature of an individual viewing said display to produce sampled peripheral skin temperature data; and an image obscuration circuit for obscuring an image from said image source displayed on said display, wherein said obscuration of said displayed image is functionally related to said sampled peripheral skin temperature.

9. The system of claim 8 wherein said display is an electronic display and said image source is a source of electronic images.

10. The system of claim 8 wherein said device includes a sensor for sensing the skin temperature of at least one extremity of a said individual.

11. The system of claim 8 wherein said device includes a sensor for sensing the skin temperature of at least one finger of said individual.

12. The method of claim 8 including earphones adapted to be worn by said individual and further including an audio circuit for providing obscured audio related to said displayed image to said earphones, wherein said obscured audio is functionally related to said sampled peripheral skin temperature.

13. A method of determining whether an individual has Attention Deficit Hyperactivity Disorder (ADHD) comprising:

displaying an image, having a level of obscuration, to an individual for a predetermined time interval when said individual is in an inactive state;

sampling the peripheral skin temperature of said individual to provide sampled peripheral skin temperature data; and analyzing the sampled peripheral skin temperature data for a pre-selected parameter, to determine whether said has a value indicative of ADHD.

14. The method of claim 13 wherein the skin temperature of at least one extremity of said individual is sampled.

15. The method of claim 13 wherein the skin temperature of at least one finger of said individual is sampled.

16. The method of claim 13 including providing obscured audio related to the displayed image to said individual.

17. The method of claim 16 wherein said audio is provided to said individual by earphones worn by said individual.

* * * * *